(12) United States Patent
Hopermann et al.

(10) Patent No.: US 7,966,064 B2
(45) Date of Patent: Jun. 21, 2011

(54) MEDICAL SYSTEM WITH GALVANIC SEPARATION

(75) Inventors: Hermann Hopermann, Badendorf (DE); Klaus Glindemann, Stockelsdorf (DE)

(73) Assignee: Dräger Medical GmbH, Lübeck (DE)

( * ) Notice: Subject to any disclaimer, the term of this patent is extended or adjusted under 35 U.S.C. 154(b) by 594 days.

(21) Appl. No.: 12/041,080

(22) Filed: Mar. 3, 2008

(65) Prior Publication Data
US 2008/0281380 A1 Nov. 13, 2008

(30) Foreign Application Priority Data
May 12, 2007 (DE) .......................... 10 2007 022 286

(51) Int. Cl.
*A61N 1/08* (2006.01)
(52) U.S. Cl. ................. 607/2; 607/34; 607/61
(58) Field of Classification Search ........ 607/34
See application file for complete search history.

(56) References Cited

U.S. PATENT DOCUMENTS
3,195,540 A * 7/1965 Waller ........................... 607/33
7,587,241 B2 * 9/2009 Parramon et al. ............... 607/16
2005/0113887 A1 * 5/2005 Bauhahn et al. ................ 607/61

FOREIGN PATENT DOCUMENTS
DE  38 13 868 A1  12/1988
* cited by examiner

*Primary Examiner* — Kennedy J Schaetzle
(74) *Attorney, Agent, or Firm* — McGlew & Tuttle, P.C.

(57) ABSTRACT

A medical system with a medical device and with a supply unit. The supply unit is designed to be separably connected to the medical device and to supply the medical device with electric energy without interruption. The medical system has an isolating transformer and a changeover device, wherein the changeover device is connected to the isolating transformer and to the medical device and is designed to connect the medical device or the supply unit to an electric supply network via the isolating transformer as desired.

20 Claims, 9 Drawing Sheets

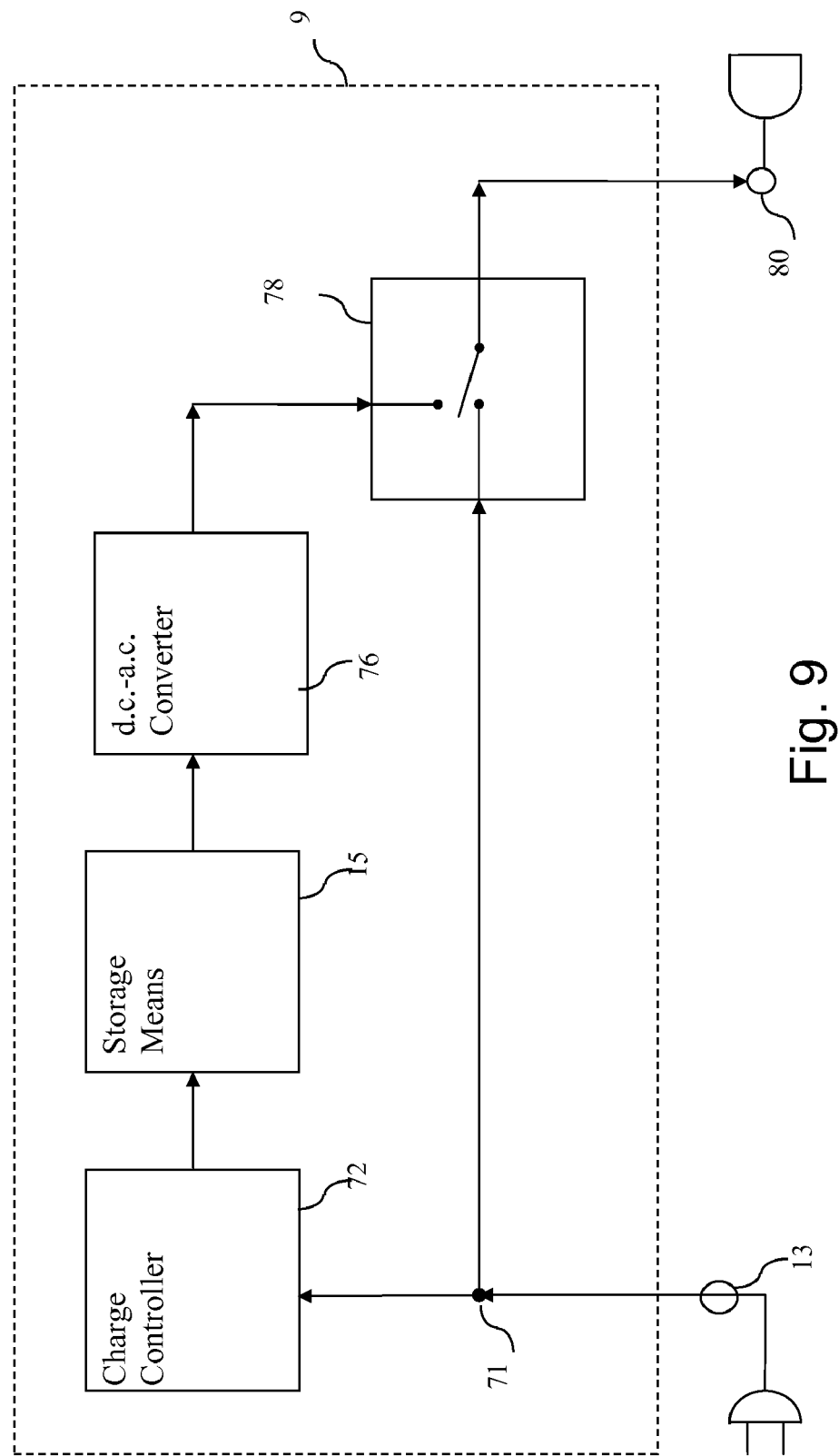

MEDICAL SYSTEM WITH GALVANIC SEPARATION

CROSS REFERENCE TO RELATED APPLICATIONS

This application claims the benefit of priority under 35 U.S.C. §119 of German Patent Application DE 10 2007 022 286.8 filed May 12, 2007, the entire contents of which are incorporated herein by reference.

FIELD OF THE INVENTION

The present invention pertains to a medical system with at least one medical device and with a supply unit. The supply unit is designed to be detachably connected to the medical device and to supply the medical device with electric energy without interruption.

BACKGROUND OF THE INVENTION

Medical systems known from the state of the art with a medical device and with a supply unit have an isolating transformer for connection to an electric supply network. The isolating transformer causes a galvanic separation of the medical device or the supply unit from the supply network. Electric leakage currents are reduced hereby.

An interruption-free power supply unit, which can be connected to an electric supply network, is known from DE 38 138 68 A1. The interruption-free power supply unit has a frequency converter and an isolating transformer. The isolating transformer has a third winding, which is isolated from an input winding and an output winding and which is connected to a power converter, whose d.c. side is connected to a backup battery.

SUMMARY OF THE INVENTION

The basic object of the present invention is to propose an improved medical system with a medical device with an interruption-free power supply for the medical device. This object is accomplished by a medical system of the type described in the introduction. The medical system has an isolating transformer and a changeover device, wherein the changeover device is connected to the isolating transformer and the medical device and is designed to connect the medical device or the supply unit to an electric supply network via the isolating transformer as desired. Due to the changeover device, the isolating transformer can be advantageously used by both the medical device and the supply unit in order to galvanically separate the medical system from the electric supply network.

The medical device is preferably a mobile medical device or the supply unit is a mobile supply unit or both are of a mobile design. A mobile medical device or a mobile supply unit is designed, furthermore, as a portable unit and can be arranged, for example, in the vicinity of a patient bed or connected to a patient bed.

In an advantageous embodiment, a mobile supply unit and/or a mobile medical device may have wheels for transporting. The medical system may preferably have an interface for separable electrical connection for separably connecting the medical device to the supply unit. The interface may be formed, for example, by a patch plug. The supply unit may be designed, for example, preferably as a docking station. As a result, the medical device can be connected to the supply unit electrically and preferably mechanically in a positive-locking and/or non-positive manner.

In a preferred embodiment, the medical device has an isolating transformer. As a result, the medical device can be advantageously connected to a supply network independently from the supply unit.

In a preferred embodiment, the medical device has a network input for connection to a supply network, and the changeover device is designed to connect the isolating transformer on the output side at least indirectly to the medical device or to the supply unit as desired. As a result, the medical device can be connected to a supply network independently from the supply unit.

In an advantageous embodiment, the supply unit has a power supply unit for supplying the medical device with power without interruption and a network input for connection to a supply network. In a likewise preferred manner, the changeover device is designed to connect the network input of the supply unit at least indirectly to the isolating transformer or to the power supply unit as desired.

In an advantageous embodiment of the medical system, the isolating transformer has a primary winding and a secondary winding, which are magnetically coupled with one another and wherein the primary winding is intended for being connected to the electric supply network and the secondary winding is intended for being connected to the supply unit or to the medical device. The medical system can thus be advantageously separated galvanically from the electric supply network.

In a preferred embodiment, the supply unit has at least one energy storage means for electric energy and is designed to detect a line voltage of the supply network and to send the electric energy being stored in the energy storage means as a function of the detected line voltage of the supply network. The energy storage means may be advantageously a rechargeable battery, for example, a capacitor, a lead gel battery, a lithium-ion battery, a lithium-polymer battery or a nickel-cadmium battery or a nickel-metal hydride battery.

In a likewise preferred manner, the supply unit has a frequency changer, especially an inverse rectifier, which is designed to convert electric energy, which is being stored in the energy storage means, for example, a rechargeable battery, and is sent as a d.c. voltage, into an a.c. voltage. The a.c. voltage can then is used to supply the medical device with electric energy.

In a preferred embodiment, the changeover device has at least two changeover switches. For example, the changeover device may have a first changeover switch and a second changeover switch. The first changeover switch is preferably connected to the medical device and the second changeover switch to the supply unit. The first changeover switch and the second changeover switch are connected to one another separably, for example, by means of an interface.

The medical device may have for this purpose an interface connected to the first changeover switch for connection to the supply unit, and the supply unit may have an interface connected to the second changeover switch for connection to the medical device.

The changeover device may preferably have a detection device, which can detect the fact that the medical device is connected to the supply unit and activate the changeover device, especially the first and/or second changeover switch, for switching over as a function of the connection. The first changeover switch, hereinafter also called changeover switch of the medical device, is preferably designed to connect the isolating transformer depending on whether the interface is connected optionally to the electric supply network, especially to a terminal for the electric supply network, or to the interface for connection to the supply unit.

The changeover device preferably has a detection device for detecting a line voltage, which can detect the presence of a line voltage and is designed to activate the changeover device, especially the first and/or second changeover switch, for switching over as a function of the detected line voltage.

The changeover switch of the medical device is designed, for example, to connect the network input of the medical device to the interface or to the isolating transformer, and there preferably to a secondary winding of the isolating transformer, as desired, depending on the connection of the interface and/or depending on a detected line voltage.

The second changeover switch, hereinafter also called changeover switch of the supply unit, is preferably designed to connect the power supply unit of the supply unit to the network terminal of the supply unit or at least indirectly to the isolating transformer and via the isolating transformer to the electric supply network as desired, depending on the connection of the interface and/or depending on a detected line voltage.

In an advantageous embodiment, which is favorable in terms of effort, a changeover switch may have galvanic contacts. In addition or independently from galvanic contacts, a changeover switch may advantageously have at least one switching transistor, a thyristor and/or a TRIAC.

The present invention also pertains to a process for supplying a medical device with electric energy, in which the energy is supplied from an electric supply network in a galvanically separated manner, and in which a supply unit with an energy storage means supplies electric energy without interruption. The supply unit is electrically connected in this process to the supply network via the isolating transformer depending on an electrical or additionally mechanical connection of the medical device to the supply unit.

The present invention will be described below on the basis of figures and additional exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 9 is a schematic view showing an exemplary embodiment of a power supply unit for interruption-free power supply.

DESCRIPTION OF THE PREFERRED EMBODIMENTS

Figure 1:
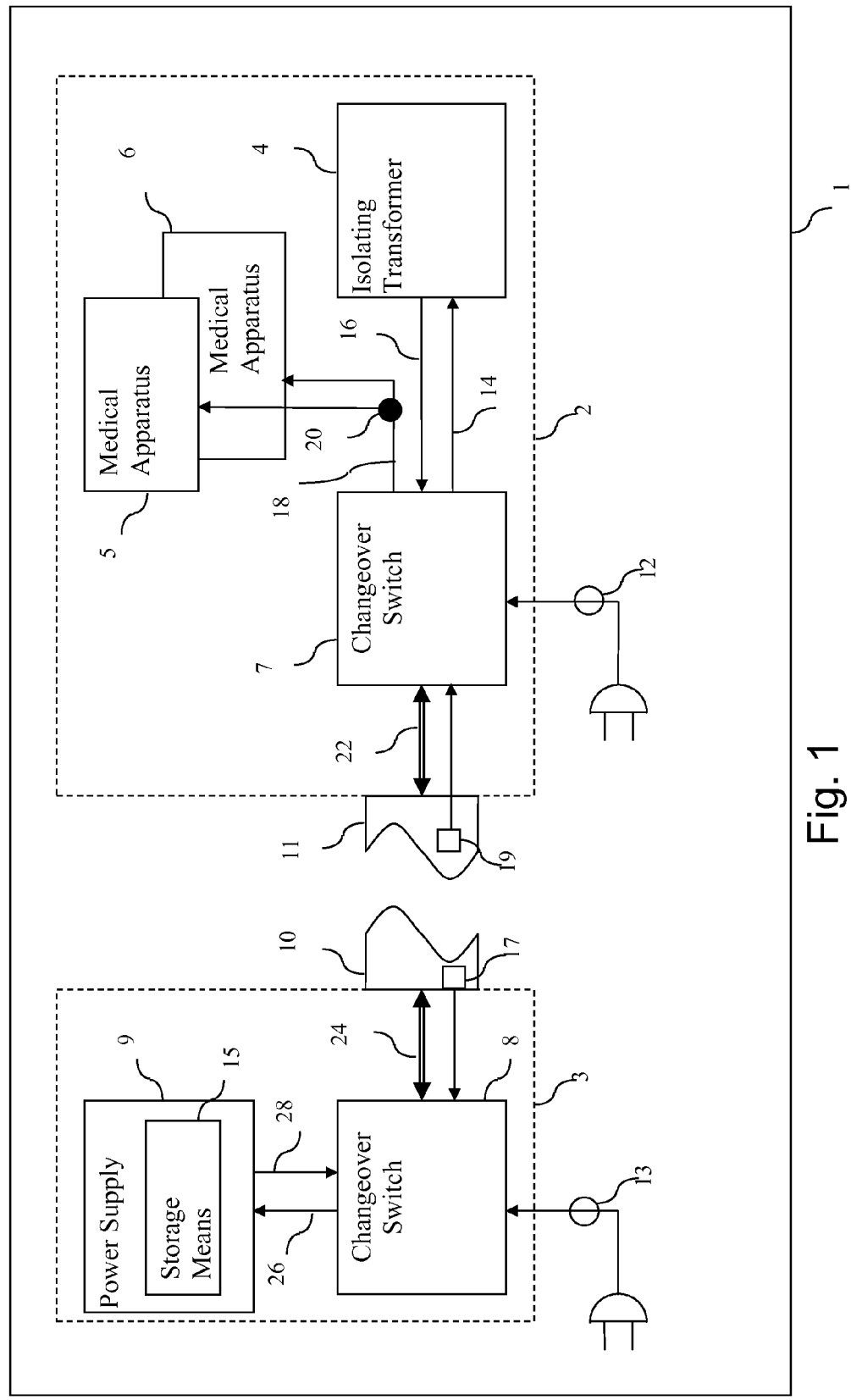
FIG. 1 is a schematic view showing an exemplary embodiment of a medical system with a supply unit and a medical device according to the invention.

Referring to the drawings in particular, FIG. 1 schematically shows an exemplary embodiment of a medical system 1. The medical system 1 comprises a medical device 2 and a supply unit 3. The medical device 2 has an isolating transformer 4, and at least one medical apparatus, in this embodiment, as an example, a medical apparatus 5 and a medical apparatus 6. The medical device 2 also has a changeover switch 7. The supply unit 3 has a changeover switch 8. The supply unit 3 also has a power supply unit 9. The power supply unit 9 is designed to supply the medical device 2, especially the medical apparatus 5 and 6, with power without interruption. The supply unit 3 has an interface 10 and the medical device 2 has an interface 11, the interface 10 and the interface 11 being designed each for being connected to one another electrically or additionally mechanically, especially in a positive-locking and/or non-positive manner. The interfaces 10 and 11 may have, for example, a plurality of electric contacts, especially plug-type contacts each. The changeover switch 7 and the changeover switch 8 form together a changeover device of the medical system 1 in this exemplary embodiment. The medical device 2 has a network terminal 12, which is provided for connecting the medical device 2 to a power supply network. The network terminal 12 is connected to the changeover switch 7.

The supply unit 3 has a network terminal 13, which is intended for connection to an electric supply network and is connected to the changeover switch 8. The changeover switch 7 is connected on the output side to the isolating transformer 4 via a connection line 14. The isolating transformer 4, especially a primary winding of the isolating transformer 4, is connected on the input side to the connection line 14. The isolating transformer 4, especially a secondary winding of the isolating transformer 4, is connected on the output side to the changeover switch 7 via a connection line 16. The changeover switch 7 is connected on the output side to a connection node 20 via a connection line 18. The medical apparatus 5 and the medical apparatus 6 are electrically connected each to the connection node 20 for picking up current. The changeover switch 7 is connected to the interface 11 via a connection 22.

Connection 22 may have a plurality of connection lines and may be designed, for example, as a connection bus. The changeover switch 8 is connected to the interface 10 via a connection 24. Connection 24 may have a plurality of connection lines and may be designed, for instance, as a connection bus. The changeover switch 8 is connected on the output side to the power supply unit 9 via a connection line 26. The power supply unit 9 is connected on the output side to the changeover switch 8 via a connection line 28.

The changeover switch 8 is designed to detect a line voltage present at the network input 13 and is designed, furthermore, to connect the network input 13 to the interface 10 or via the connection line 26 to the power supply unit 9 as desired, depending on the detected line voltage and/or depending on whether the interface 11 is connected to the interface 10. In case the interface 10 is separated from the interface 11, an energy storage means 15 of the power supply unit 9, for example, a rechargeable battery, can be charged. The changeover switch 7 is designed to detect a line voltage present at the network input 12 and to connect the isolating transformer 4 on the input side to the network terminal 12 or to the interface 11 for indirect connection to the network terminal 13 or the power supply unit 9 as desired, depending on the detected line voltage and/or depending on whether the interface 10 is connected to the interface 11. The changeover switch 7 is designed, furthermore, to connect the isolating transformer 4 on the output side to the interface 11 or to the connection node 20—and thus to the medical apparatus 5 and to the medical apparatus 6, as desired, depending on whether the interface 10 is connected to the interface 11. The changeover device 7 and the changeover device 8 may be connected on the input side to a connection sensor 17 and 19, respectively, for detecting the connection of the interfaces 10 and 11, and change over depending on the connection sensor signal. The connection sensor 17 and/or 19 may be, for example, an optical, magnetic or mechanical sensor.

Figure 2:
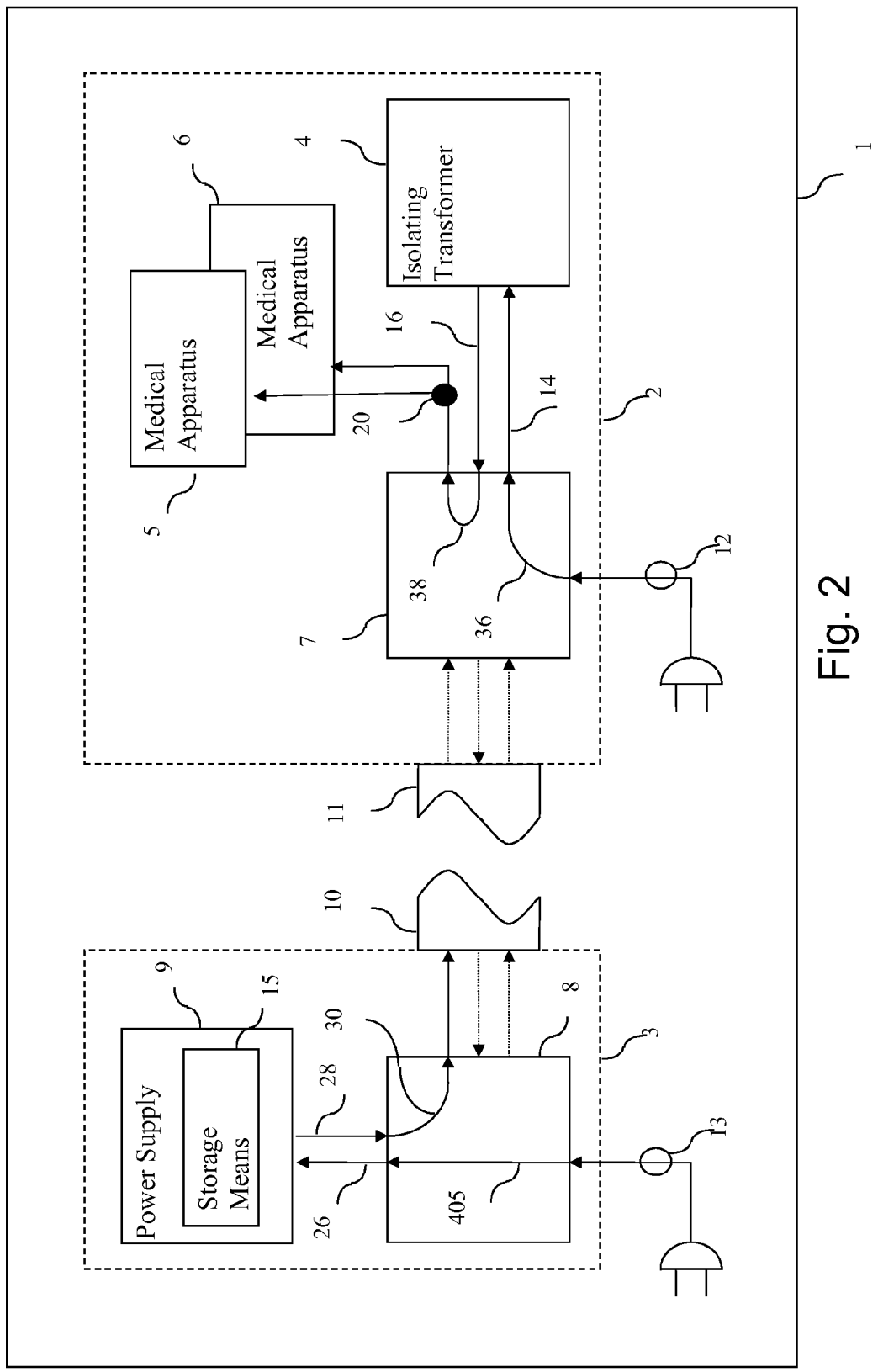
FIG. 2 is a schematic view showing the medical system shown in FIG. 1, in which the supply unit and the medical device are separated from each other and the supply unit and the medical device carry line voltage each.

FIG. 2 schematically shows the medical system shown in FIG. 1, in which the interfaces 10 and 11 are separated from each other and the network input 12 and the network input 13 carry a line voltage each. The changeover switch 8 of the supply unit 3 connects the network input 13 to the power supply unit 9 via a current path 40 and the connection line 26. An energy storage means 15 of the power supply unit 9 can thus be charged. The power supply unit 9 is connected on the output side to the interface 10 via the connection line 28 and via the current path 30. The power supply unit 9 is thus ready to send electric energy via the interface 10. The isolating transformer 4 is connected on the output side to the connection node 20 via a current path 38. The network input 12 is connected to the isolating transformer 4 and there especially to a primary winding by means of the changeover switch 7 via a current path 36 and via the connection line 14.

Figure 3:
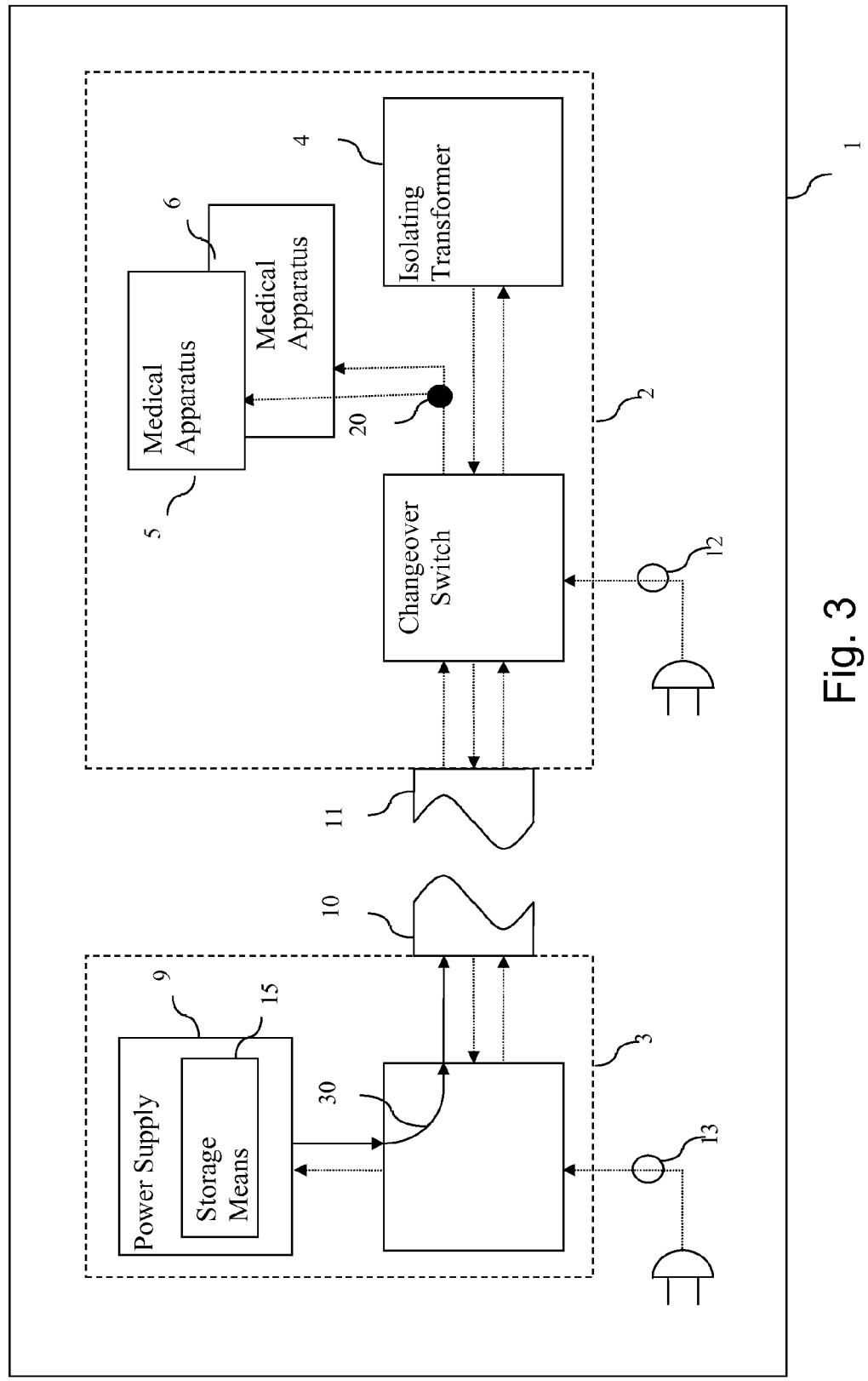
FIG. 3 is a schematic view showing the medical system shown in FIG. 1, in which the supply unit and the medical device are separated from each other and the supply unit is ready to send electric energy.

FIG. 3 schematically shows the medical system shown in FIG. 1, in which the interfaces 10 and 11 are separated from each other and in which the network input 12 and the network input 13 carry no line voltage. The supply unit 3 is ready in this circuitry example to send electric energy via the current path 30 from the power supply unit 9 and there from the storage means 15 at the interface 10.

Figure 4:
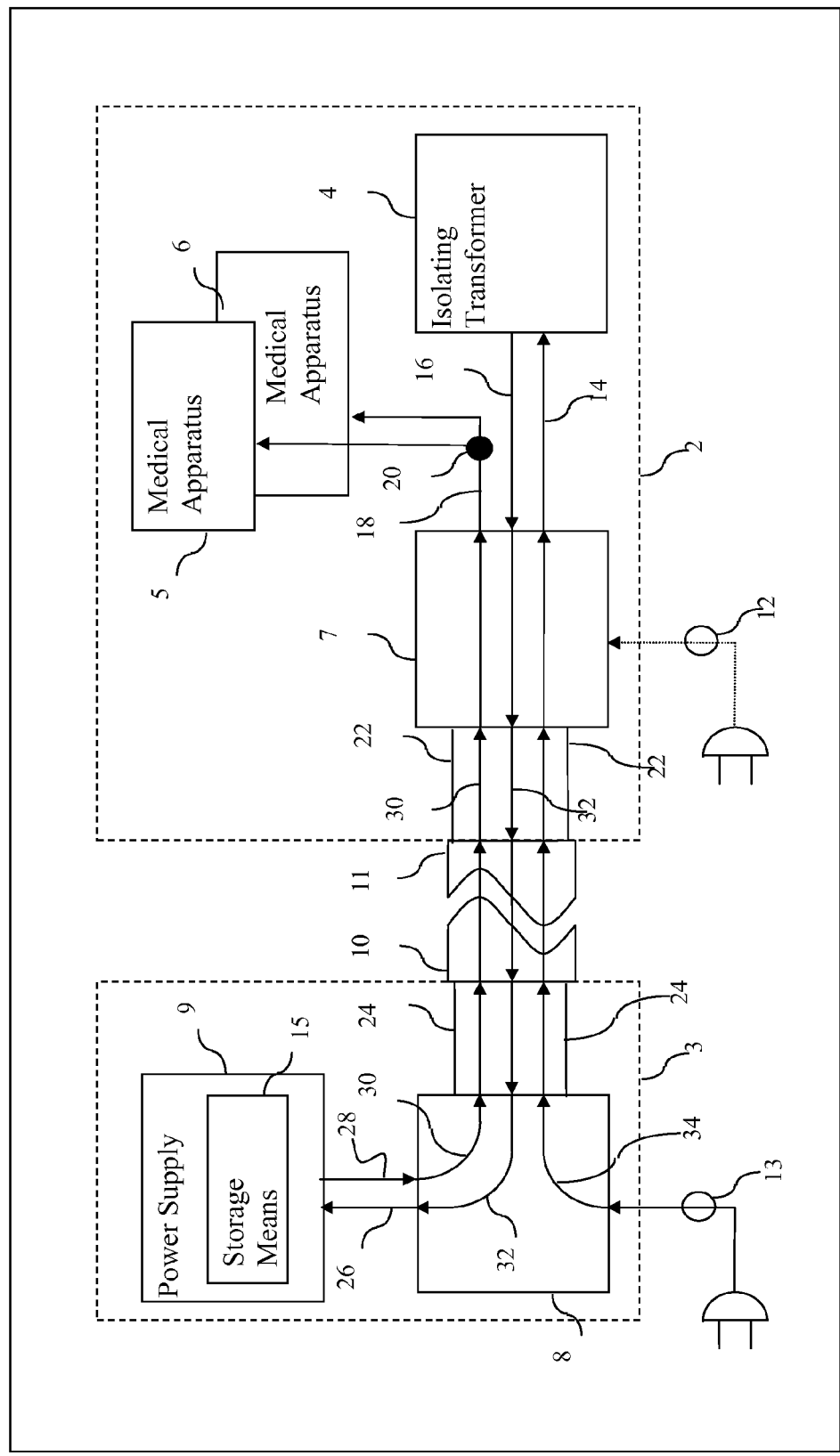
FIG. 4 is a schematic view showing the medical system shown in FIG. 1, in which the supply unit and the medical device are connected to one another and a network input of the supply unit carries a line voltage.

FIG. 4 schematically shows the medical system shown in FIG. 1, in which the network input 13 carries a line voltage and the network input 12 carries no line voltage. Interface 10 and interface 11 are electrically or additionally mechanically connected to one another in this circuitry example. The network input 13 is connected in this circuitry example to the isolating transformer 4 and there, especially on the input side, to a primary winding of the isolating transformer 4 via a current path 34, passing through the connection 24, interfaces 10 and 11, connection 22, changeover switch 7 and connection line 14. The isolating transformer 4 is connected on the output side indirectly to a network input of the power supply unit 9 via a current path 32. The current path 32 passes over the connection line 16, changeover switch 7, connection 22, interfaces 11 and 10, connection 24, changeover switch 8 and connection line 26. The power supply unit 9 is connected in the circuitry example to the connection node 20 and hence indirectly to the medical apparatuses 5 and 6 via the current path 30. Current path 30 passes in this circuitry example via the connection line 28, changeover switch 8, connection 24, interfaces 10 and 11, connection 22, changeover switch 7, connection line 18, and connection node 20 to the medical apparatuses 5 and 6.

Figure 5:
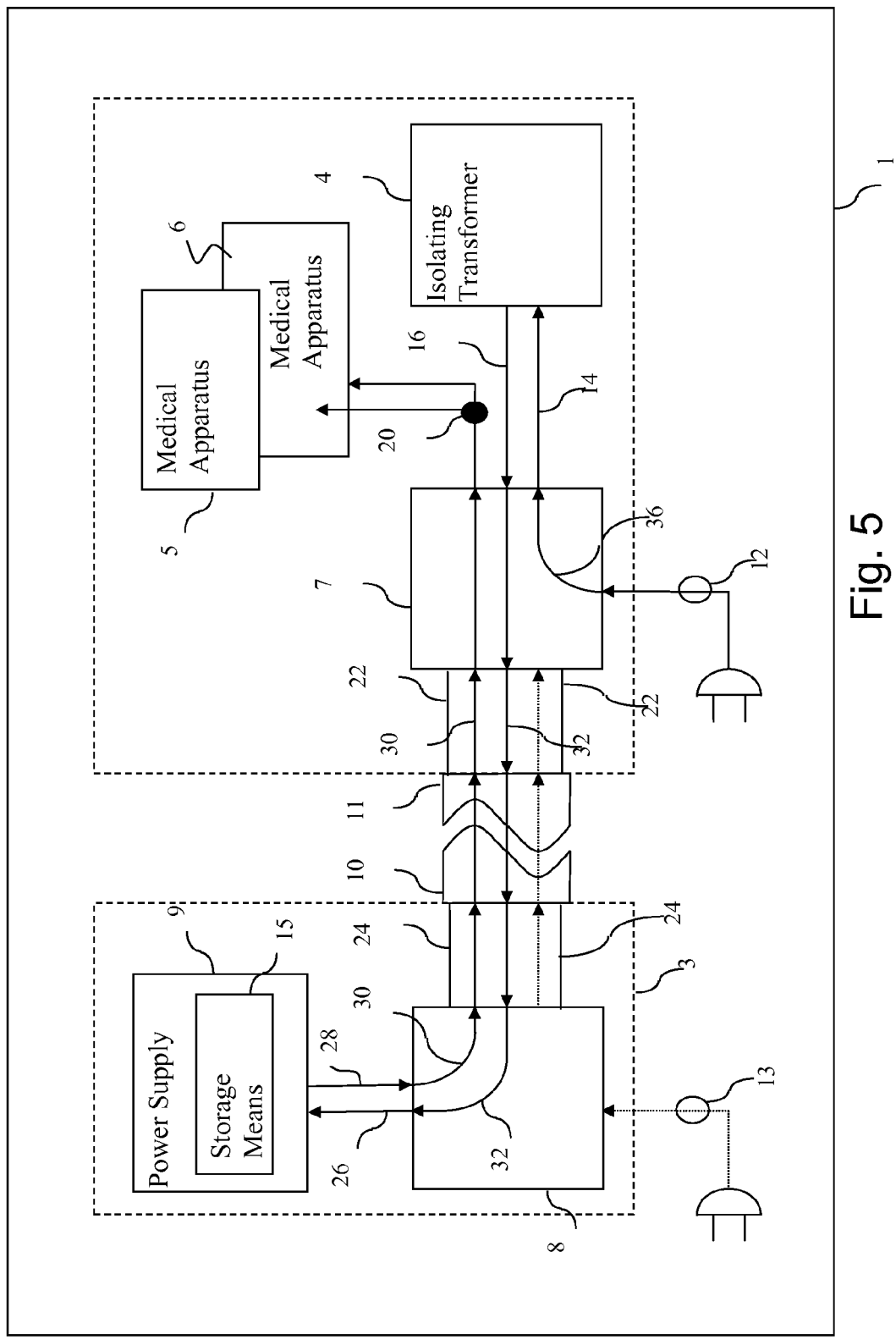
FIG. 5 is a schematic view showing an example of the circuitry of the medical system shown in FIG. 1, in which system a line voltage is present at the network input of the medical device and a network input of the supply unit carries no line voltage.

FIG. 5 schematically shows a circuitry example of the medical system shown in FIG. 1, in which the network input 12 carries a line voltage and network input 13 carries no line voltage. The interfaces 10 and 11 are electrically or additionally mechanically connected to one another in this circuitry example. Network input 12 is connected to the input of the isolating transformer 4 via the current path 36. Current path 36 passes over the changeover switch 7 and the connection line 14. The isolating transformer 4 is connected on the output side to the network input of the power supply unit 9 via the current path 32. The power supply unit 9 is connected on the output side to the connection node 20 via current path 30 and thus indirectly to the medical apparatuses 5 and 6. The medical apparatuses 5 and 6 are thus secured against failure of the network by means of the power supply unit 9 and the medical system 1 is galvanically separated by means of the isolating transformer 4 from the electric supply network connected to the network input 12.

Figure 6:
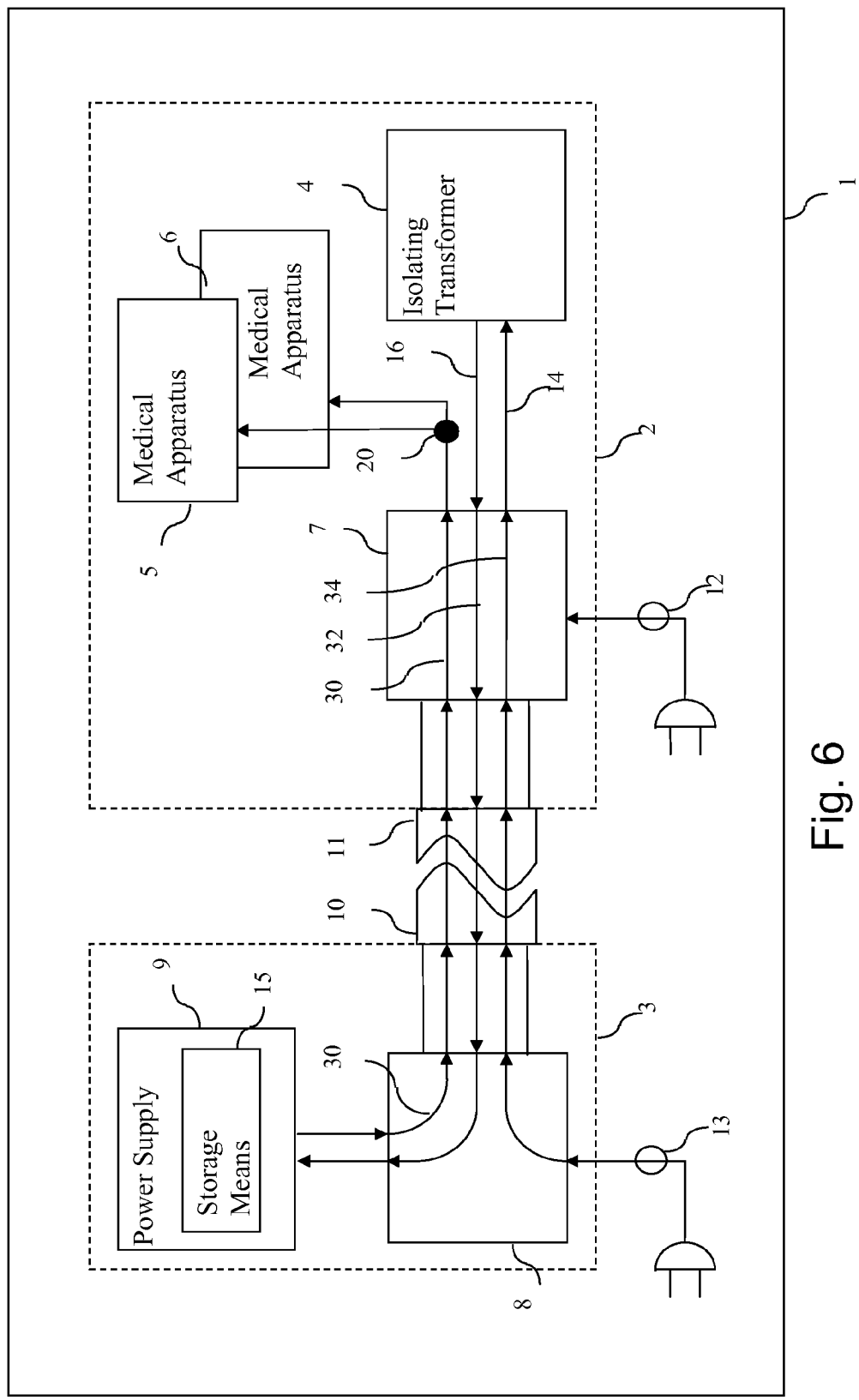
FIG. 6 is a schematic view showing an example of the circuitry of the medical system shown in FIG. 1, in which system the supply unit and the medical device are connected to one another and a line voltage is present on the supply unit and the medical device.

FIG. 6 schematically shows a circuitry example of the medical system shown in FIG. 1, in which network input 12 and network input 13 carry a line voltage each and in which the interfaces 10 and 11 are electrically or additionally mechanically connected to one another. The changeover device, formed from the changeover switches 7 and 8, is designed in this exemplary embodiment to receive the line voltage via the network input 13 in case the interface 10 is connected to interface 11 and in case a line voltage is present at the network input 12 and at the network input 13. The embodiment variant shown in FIG. 5 above, in which a line voltage is received via the network input 12, is conceivable as well. Network input 13 is indirectly connected to the input of the isolating transformer 4 via the current path 34. Current path 34 passes over the changeover switch 8, interfaces 10 and 11, changeover switch 7 and the connection lines located in between, which were already described above. The isolating transformer 4 is connected on the output side to the network input of the power supply unit 9 via current path 32. The power supply unit 9 is connected on the output side to the connection node 20 via current path 30 and thus indirectly to the medical apparatuses 5 and 6.

Figure 7:
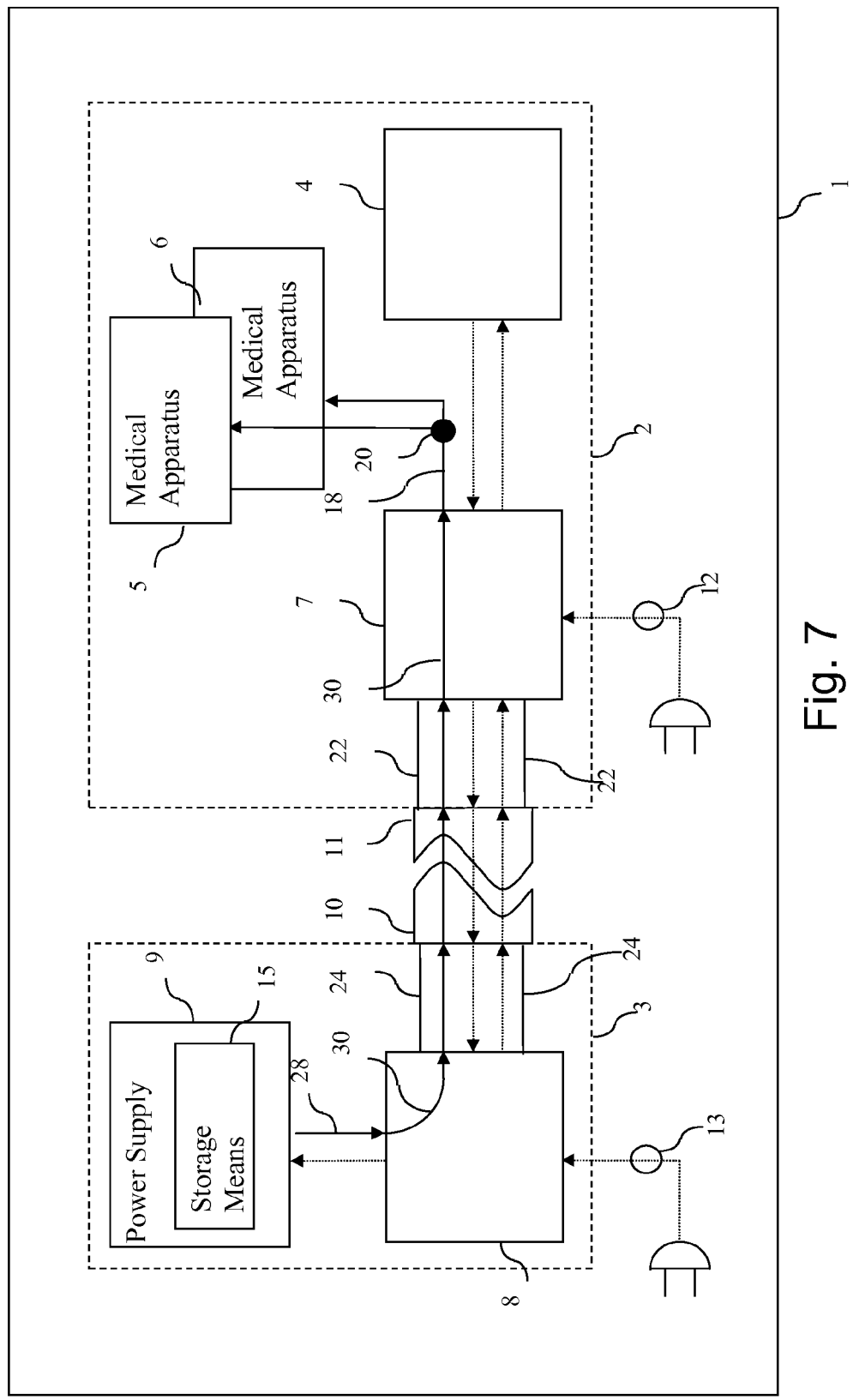
FIG. 7 is a schematic view showing an example of the circuitry of the medical system shown in FIG. 1, in which the supply unit and the medical device are connected to one another and the medical device is supplied by the supply unit with stored electric energy.

FIG. 7 schematically shows a circuitry example of the medical system shown in FIG. 1, in which the network inputs 12 and 13 carry no voltage and the medical apparatuses 5 and 6 are supplied with electric energy from the power supply unit and thereby the energy storage means 15. The interfaces 10 and 11 are electrically or additionally mechanically connected to one another in this circuitry example. The power supply unit 9 is connected on the output side to the connection node 20 and hence to the medical apparatuses 5 and 6 via the current path 30 indirectly, namely, via the connection line 28, changeover switch 8, connection 24, interfaces 10 and 11, connection 22, changeover switch 7 and connection line 18.

Figure 8:
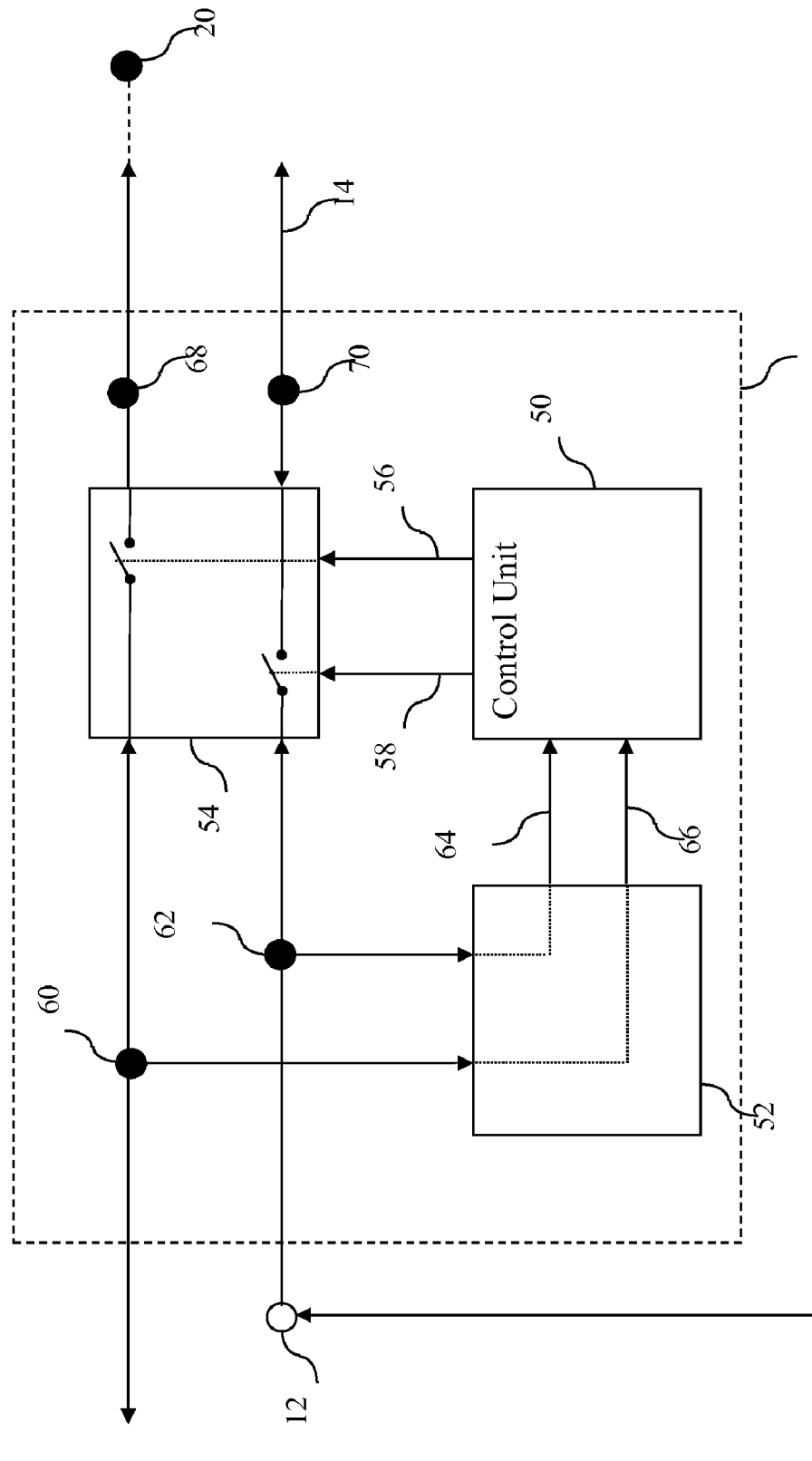
FIG. 8 is a schematic view showing an exemplary embodiment of a changeover device.

FIG. 8 schematically shows an exemplary embodiment of the changeover switch shown in FIGS. 1 through 7. The changeover switch 7 has a control unit 50, a voltage recognition unit 52 and a switch, especially a power switch 54. The control unit 50 is connected on the output side to the switch 54 via a control line 56 and via a control line 58. Switch 54 is designed in this exemplary embodiment as a multiple switch and has, for example, two switches for switching one connection path each, of which a first switch is functionally connected to the control line 56 and a second switch is functionally connected to the control line 58. The voltage detection unit 52 is connected on the input side to a connection node 60, which is functionally connected to the interface 11 shown in FIG. 1. Connection node 60 is connected to switch 54 and is connected via switch 54—controllable via the control line 56—to an output for the medical apparatuses 5 and 6 shown in FIG. 1. The voltage recognition unit 52 is designed to generate a line voltage signal for controlling the control unit 50 depending on a line voltage detected on the input side and to send this on the output side. The voltage recognition unit 52 is of a two-channel design in this embodiment. In case of a line voltage present at the connection node 60, the voltage recognition unit 52 can send a line voltage signal to the control unit 50 via the connection line 66 and in case of a detected line voltage at the connection node 62 to the voltage recognition unit 52, it can send a line voltage signal to the control unit 50 via the connection line 64.

Depending on a line voltage signal detected on the input side, the control unit 50 can generate a control signal for actuating the switch 54 and send this on the output side. The changeover switch 7 shown in FIG. 1 is shown only partially in FIG. 8. The changeover switch shown in FIG. 7 is additionally designed to connect the output of the isolating transformer 4 to the connection node 20 and to separate the connection node 20 for this from the interface 11.

FIG. 9 schematically shows an exemplary embodiment of the power supply unit 9 shown in FIG. 1. The power supply unit 9 has a network output 13 for connecting a supply network, an energy storage means 15, a charge controller 72 for charging the energy storage means 15, a d.c.-a.c. converter 76 and a changeover switch 78. The changeover switch 78 is connected on the input side to the network input 13 via a connection node 71. The connection node 71 is connected to a line voltage input of the charge controller 72. The charge controller 72 is connected to the energy storage means 15 on the output side. The energy storage means 15 is connected to the d.c.-a.c. converter 76. The d.c.-a.c. converter 76 is connected to the changeover switch 78 on the a.c. side. Changeover switch 78 is designed to detect a line voltage present at the network input 13 and thus at the connection node 71 and to connect the connection node 71 or the a.c. output of the d.c.-a.c. converter 76 to an output 80 of the power supply unit as desired depending on the detected line voltage.

The energy storage means 15 may be, for example, a capacitor, a lead gel battery, a lithium ion battery, a lithium-polymer battery, or a nickel-cadmium battery or a nickel-metal hydride battery.

While specific embodiments of the invention have been shown and described in detail to illustrate the application of the principles of the invention, it will be understood that the invention may be embodied otherwise without departing from such principles.

What is claimed is:

1. A medical system comprising:
   a medical device;
   a supply unit separably connected to said medical device at a physical interface to supply said medical device with electric energy without interruption;
   an isolating transformer; and
   a changeover device, said changeover device being connected at least indirectly to said isolating transformer and to said medical device, said changeover device for connecting said medical device to an electric supply network via said isolating transformer and for connecting said supply unit to the electric supply network via said isolating transformer as desired.

2. A medical system in accordance with claim 1, wherein said isolating transformer is a part of a unit comprising said medical device.

3. A medical system in accordance with claim 1, wherein said medical device has a network input for connection to the supply network, and said changeover device connects said isolating transformer on an output side at least indirectly to said medical device or to said supply unit as desired.

4. A medical system in accordance with claim 1, wherein said supply unit has a power supply unit for supplying said medical device with power without interruption and a network input for connection to the supply network, and said changeover device is designed to connect said network input of said supply unit at least indirectly to said isolating transformer or to said power supply unit.

5. A medical system in accordance with claim 1, wherein said changeover device has a first changeover switch and a second changeover switch, wherein said first changeover switch is connected to said medical device and said second changeover switch is connected to said supply unit.

6. A medical system in accordance with claim 5, further comprising an interface wherein said first changeover switch and said second changeover switch are separably connected to one another by means of said interface, and a medical device interface side is connected to said first changeover switch for connection to said supply unit and a supply unit interface side is connected to said second changeover switch for connection to said medical device.

7. A medical system in accordance with claim 1, wherein said supply unit has an energy storage means for storing electric energy and detecting a line voltage of the electric supply network and to sending electric energy stored in said energy storage means depending on the detected line voltage.

8. A medical system in accordance with claim 1, wherein said isolating transformer has a primary winding and a secondary winding, wherein said primary winding is connected to the electric supply network and said secondary winding connected to said supply unit or said medical device.

9. A medical system comprising:
   a medical device;
   a supply unit separably connected to said medical device to supply said medical device with electric energy without interruption;
   an isolating transformer; and
   a changeover device, said changeover device being connected at least indirectly to said isolating transformer and to said medical device, said changeover device for connecting said medical device and said supply unit to an electric supply network via said isolating transformer as desired, wherein said changeover device has a detection device designed to detect when said medical device is connected to said supply unit and to activate said changeover device for changing over depending on a connection state.

10. A medical system comprising:
    a medical device;
    a supply unit separably connected to said medical device to supply said medical device with electric energy without interruption;
    an isolating transformer; and
    a changeover device, said changeover device being connected at least indirectly to said isolating transformer and to said medical device, said changeover device for connecting said medical device and said supply unit to an electric supply network via said isolating transformer as desired wherein said changeover device has a detection device for detecting a line voltage, said detection device detecting a presence of a line voltage and activating said changeover device for changing over depending on the detected line voltage.

11. A process for supplying a medical device with electric energy, the process comprising the steps of:
providing a medical device with a network input for connection to an electric supply network;
providing a supply unit with a network input for connection to the electric supply network, said supply unit being separably connected to said medical device by a physical interface to supply said medical device with electric energy without interruption;
providing an isolating transformer;
providing a changeover device, said changeover device being connected at least indirectly to said isolating transformer and to said medical device; and
using said changeover device for connecting said medical device to the electric supply network via said isolating transformer and for connecting said supply unit to the electric supply network via said isolating transformer depending on an electrical or additionally mechanical connection of said medical device to said supply unit to supply energy from at least one electric supply network in a galvanically separated manner.

12. A process in accordance with claim 11, wherein said isolating transformer is a part of a unit comprising said medical device.

13. A process in accordance with claim 11, said changeover device connects said isolating transformer on an output side at least indirectly to said medical device or to said supply unit as desired.

14. A process in accordance with claim 11, wherein said supply unit has a power supply unit for supplying said medical device with power without interruption and a network input for connection to the supply network, and said changeover device connects said network input of said supply unit at least indirectly to said isolating transformer or to said power supply unit.

15. A process in accordance with claim 11, wherein said changeover device has a first changeover switch and a second changeover switch, wherein said first changeover switch is connected to said medical device and said second changeover switch is connected to said supply unit.

16. A process in accordance with claim 15, further comprising providing an interface wherein said first changeover switch and said second changeover switch are separably connected to one another by means of said interface, and a medical device interface side is connected to said first changeover switch for connection to said supply unit and a supply unit interface side is connected to said second changeover switch for connection to said medical device.

17. A process in accordance with claim 11, wherein said changeover device has a detection device designed to detect whether said medical device is connected to said supply unit and to activate said changeover device for changing over depending on a connection state.

18. A process in accordance with claim 11, wherein said changeover device has a detection device for detecting a line voltage, said detection device detecting a presence of a line voltage and activating said changeover device for changing over depending on the detected line voltage.

19. A process in accordance with claim 11, wherein said supply unit has an energy storage means for storing electric energy and detecting a line voltage of the supply network and sending electric energy stored in said energy storage means depending on the detected line voltage.

20. A process in accordance with claim 11, wherein said isolating transformer has a primary winding and a secondary winding, wherein said primary winding is connected to the electric supply network and said secondary winding connected to said supply unit or said medical device.

* * * * *